(12) United States Patent
Ferreira

(10) Patent No.: US 11,549,929 B2
(45) Date of Patent: Jan. 10, 2023

(54) METHODS AND APPARATUS FOR DETERMINING FREE SUGAR CONTENT

(71) Applicant: Sugarwise, Inc., Lewes, DE (US)

(72) Inventor: Vinicius Thaddeu dos Santos Ferreira, Pasadena, CA (US)

(73) Assignee: Sugarwise, Inc., Lewes, DE (US)

(*) Notice: Subject to any disclaimer, the term of this patent is extended or adjusted under 35 U.S.C. 154(b) by 703 days.

(21) Appl. No.: 16/308,793

(22) PCT Filed: Jun. 8, 2017

(86) PCT No.: PCT/IB2017/053408
§ 371 (c)(1),
(2) Date: Dec. 10, 2018

(87) PCT Pub. No.: WO2017/212444
PCT Pub. Date: Dec. 14, 2017

(65) Prior Publication Data
US 2019/0257805 A1    Aug. 22, 2019

(51) Int. Cl.
*G01N 33/14* (2006.01)
*G06F 17/12* (2006.01)
(Continued)

(52) U.S. Cl.
CPC .......... *G01N 33/143* (2013.01); *G01N 33/02* (2013.01); *G01N 33/14* (2013.01); *G06F 17/12* (2013.01); *G06F 17/16* (2013.01)

(58) Field of Classification Search
CPC ...... G01N 33/02; G01N 33/14; G01N 33/143; G06F 17/12; G06F 17/16
See application file for complete search history.

(56) References Cited

U.S. PATENT DOCUMENTS

| | | | |
|---|---|---|---|
| 9,805,021 B2 * | 10/2017 | Radcliffe | G06F 40/205 |
| 2009/0105875 A1 * | 4/2009 | Wiles | A47J 31/52 |
| | | | 700/239 |

OTHER PUBLICATIONS

Franzen-Castle et al., "Adjusting Recipes to Meet Dietary Guidelines", University of Nebraska at Lincoln 2013 (Year: 2013).*
(Continued)

*Primary Examiner* — Regis J Betsch
(74) *Attorney, Agent, or Firm* — Michael D. Eisenberg

(57) ABSTRACT

We describe a method of processing data to determine a level of free sugar in a foodstuff or drink, the method comprising: inputting data defining an ingredient list for said foodstuff or drink; inputting data for an empirical analysis (b) of nutrient levels in said foodstuff or drink; inputting data defining nutrient levels for each of ingredient in said ingredient list; wherein said analysed nutrient levels (b) in said foodstuff or drink are expressible as a combination of a matrix (A) of said ingredient nutrient levels and a vector (x) defining proportions of said ingredients in said ingredient list, representing a system of simultaneous equations defining said analysed nutrient levels in terms of said ingredient proportions and ingredient nutrient levels; identifying one or more conditions selected from the group consisting of: i) a solution to said system of simultaneous equations is non-physical, ii) said system of simultaneous equations is underdetermined, and iii) said system of simultaneous equations is overdetermined; modifying said system of simultaneous equations responsive to said identifying to add one or more additional ingredients to said ingredient list, said one or more additional ingredients representing one or more ingredients contributing to sugar content of said foodstuff or drink; and determining a level of free sugar in said foodstuff or drink from said modified system of simultaneous equations.

11 Claims, 2 Drawing Sheets

(51) Int. Cl.
*G06F 17/16* (2006.01)
*G01N 33/02* (2006.01)

(56) References Cited

OTHER PUBLICATIONS

NutriData 23141 Verdugo Drive, Suite 200, Laguna Hills, CA. 92653, https://www.nutridata.com Providing nutritional analyses since 1993 (Year: 1993).*

* cited by examiner

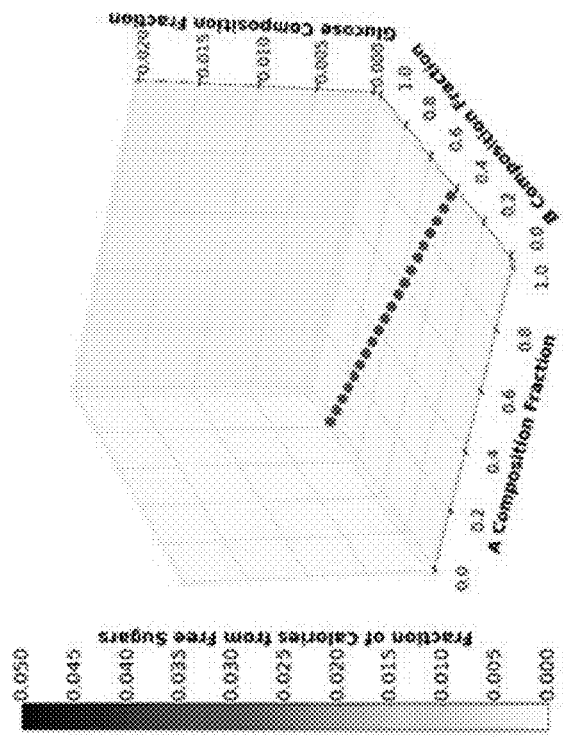
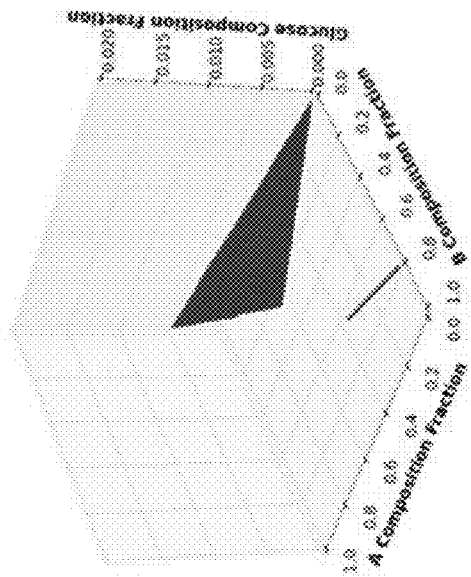
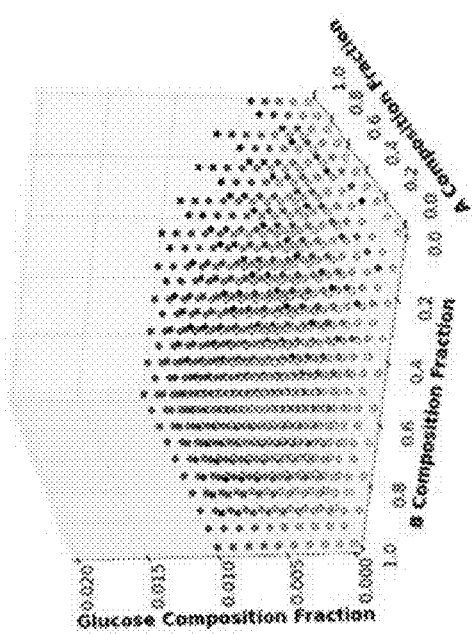
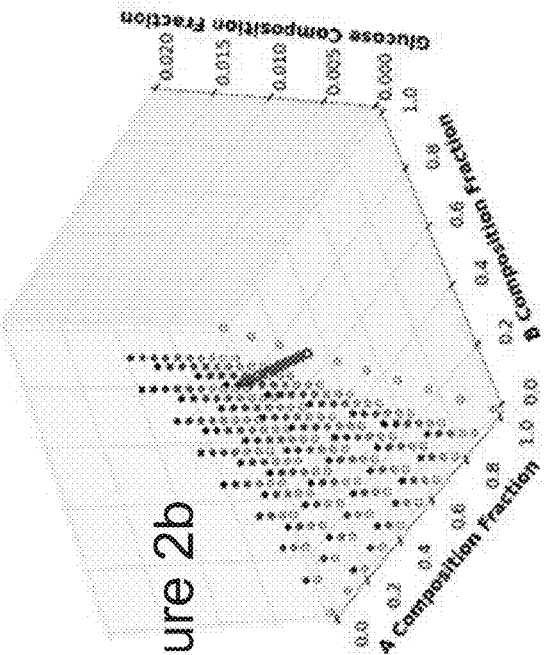
Figure 2a
Figure 2b
Figure 2c

METHODS AND APPARATUS FOR DETERMINING FREE SUGAR CONTENT

CROSS REFERENCE TO RELATED APPLICATIONS

The present application claims priority to and benefit of PCT Application PCT/IB2017/053408 entitled "Methods and Apparatus for Determining Free Sugar Content" having an international filing date of 8 Jun. 2017, which in turn claims priority to Great Britain patent application serial number 1610123.0 entitled "Methods and Apparatus for Determining Free Sugar Content" having a filing date of 10 Jun. 2016, the entire contents of which are hereby expressly incorporated by reference for all they disclose and teach.

FIELD OF THE INVENTION

This invention relates to methods, apparatus and processor control code for determining the level of free sugar, and potentially other substances, in food and drink.

BACKGROUND TO THE INVENTION

Multiple scientific studies have determined that free sugar is a leading cause of obesity, diabetes, and tooth decay. The World Health Organization has published guidelines that less than 5% of daily total consumed calories should be derived from free sugars [Guideline: "Sugars intake for adults and children", Geneva: World Health Organization; 2015]. Free sugar is classified as sugar that is derived from honey, fruit juices, and syrups, as well as added sugar in purified form, i.e. foodstuffs lacking in other nutritional content besides sugar.

However, the difference between free-sugars and non-free sugars is a categorical one, not a chemical one. Hence, chemical tests of food cannot be used to determine free sugar content directly; which precludes any attempt at analytically tested classification of foods as "low in free sugar" or otherwise. Moreover, the information currently supplied in nutritional labels is insufficient to calculate free-sugar content of food products, as no composition percentages are given. And, while composition percentages of ingredients disclosed by the manufacturer would theoretically enable such a free sugar calculation through a stoichiometric calculation, testing the validity of such manufacturer supplied information would be prohibitively expensive and time-consuming; additionally, such a calculation would not be robust against composition percentage changes during manufacturing processes.

There are currently no peer-reviewed, published methods for the empirical determination of free-sugars from laboratory measurement data. A recent attempt by the USDA to develop a database to estimate free sugar content in food products in 2012, in conjunction with the ingredient list of the product of the total sugar amount, was discontinued due to constant formulation changes of the products [Erickson, J., & Slavin, J. (2015). "Total, added, and free sugars: are restrictive guidelines science-based or achievable?", Nutrients, 7(4), 2866-2878].

Moreover, a procedure for determination of free-sugar content from analytical data was recently published in 2014 by Louie et. al. [Louie, J. C. Y., Moshtaghian, H., Boylan, S., Flood, V. M., Rangan, A. M., Barclay, A. W., & Gill, T. P. (2015), "A systematic methodology to estimate added sugar content of foods", European journal of clinical nutrition, 69(2), 154-161]. However, this method also relies on composition percentages of ingredients and requires significant subjective estimation. Therefore, this method is not thoroughly quantitative and empirical due to the need of subjective steps, depends on the willingness of the manufacturer to disclose composition information, and is prone to error due to either deliberate misreporting by the manufacturer or composition percentage changes during manufacturing processes.

There is currently no published method that leverages analytical laboratory data to determine free sugar content in food products in a way that requires no subjective estimation, is thoroughly quantitative, and does not rely on manufacturer-supplied composition percentage information. There is therefore a need for such a method, preferably one which can be used by any agency that wishes to determine if food products are below any given free sugar threshold or not.

SUMMARY OF THE INVENTION

According to the present invention there is therefore provided a method of processing data to determine a level of free sugar in a foodstuff or drink, the method comprising: inputting data defining an ingredient list for said foodstuff or drink; inputting data for an empirical analysis (b) of nutrient levels in said foodstuff or drink; inputting data defining nutrient levels for each of ingredient in said ingredient list; wherein said analysed nutrient levels (b) in said foodstuff or drink are expressible as a combination of a matrix (A) of said ingredient nutrient levels and a vector (x) defining proportions of said ingredients in said ingredient list, representing a system of simultaneous equations defining said analysed nutrient levels in terms of said ingredient proportions and ingredient nutrient levels; identifying one or more conditions selected from the group consisting of: i) a solution to said system of simultaneous equations is non-physical, ii) said system of simultaneous equations is underdetermined, and iii) said system of simultaneous equations is overdetermined; modifying said system of simultaneous equations responsive to said identifying to add one or more additional ingredients to said ingredient list, said one or more additional ingredients representing one or more ingredients contributing to sugar content of said foodstuff or drink; and determining a level of free sugar in said foodstuff or drink from said modified system of simultaneous equations.

The above described data inputting may, in each case, comprise inputting from a user, or from another computer system, or from a laboratory instrument, or from data stored in memory (either local to or remote from a processor running the method), or providing data to the procedure in any other suitable manner.

In broad terms a starting point for embodiments of the method is the recognition that, given a list of ingredients for an item of food or drink, information on the nutrients each ingredient contains, and an analysis of the nutrient levels in the food comprising the ingredients, then a system of simultaneous equations can be solved to determine the proportion of each ingredient in the food. Here "nutrients" is to be interpreted broadly; in the following description references to drink are mostly omitted for brevity, but are to be understood as included.

The system of equations may conveniently be expressed in the form of a matrix equation, where a matrix of the ingredient nutrient levels (a vector for each ingredient) operates on an unknown vector defining proportions of the ingredients, resulting in the vector defining the analysed nutrient levels. This matrix equation may then be solved for the unknown vector defining the proportions of ingredients in the food. The skilled person will appreciate that such a matrix equation may be re-arranged in many ways, but once the proportions of ingredients are known it is straightforward to determine the free sugar content of the food from the proportion of free sugar in each ingredient (which, so far as the procedure is concerned, is a given). It will be recognised that for this procedure it does not matter how free sugar is defined, merely that it is defined, and has some (known) level for each of the ingredients.

Naively one might think that this approach would be sufficient to determine the level of free sugar in food but in practice such a method, when used by itself, has significant drawbacks. Apart from the inevitable data errors it appears that there are sometimes systematic errors in the data reported by manufacturers, for example in the ingredient list. It may be that some of these errors result from systematic effects occurring during manufacture (for example fruit water content may be substantially reduced during manufacture) but a further possibility appears to be the presence of unreported added sugar. For these and other reasons the above described naïve approach will often fail but it is nonetheless desirable to be able to determine a free-sugar level in such cases, or at least to be able to determine whether or not the free-sugar level is below (or above) a threshold level, for example a health-defined threshold level.

Embodiments of the procedure identify when the system of equations does not define a unique solution to the ingredient proportions, for example because the system is underdetermined or over determined; and/or identify when a solution to the system of simultaneous equations is non-physical, for example when the solution includes a negative proportion of an ingredient or when the proportions (percentages) add up to greater than unity (more than 100%). In such cases the procedure modifies the original ingredient list to add additional ingredients representing further contributions to the sugar content of the food, in effect to postulate the presence of unreported free (added) sugar. In embodiments this adds an additional parameter which is able to vary independently of the ingredients. The system then makes a determination of the level of free sugar in the food (or drink) from this modified system of simultaneous equations.

Conveniently, but not essentially, whether or not the system of equations is under determined or overdetermined can be established by determining the rank of the matrix of ingredient nutrition levels and the rank of the augumented matrix comprised of this nutrient matrix augmented by the vector of analysed nutrient levels—a comparison of these two ranks with the number of ingredients and nutrients can be used to determine whether or not the system of equations is underdetermined (or overdetermined).

When the system of equations is underdetermined the procedure may, nonetheless, be able to determine whether or not the level of free sugar is less than (or greater than) a threshold. One embodiment of the procedure further comprise determining sets of possible values of proportions of ingredients and determining the (total) level of free sugar in each set in comparison with the free sugar level threshold. More particularly in embodiments a form of multi-dimensional surface may be defined in a number of dimensions corresponding to the number of ingredients where the surface indicates the threshold level of free sugar. Points within the surface in this space may then be defined to be within the threshold, and vice versa. In practice this may be achieved by considering each possible proportion of each ingredient (ingredient 1 at 0.00, 0.01, 0.02 whilst the remaining ingredients are all at 0, then repeating for ingredient 2 at 0.01, and so forth), for each case summing the total free sugar and determining whether or not this is above or below the threshold. In this way the threshold may be defined by a set of ingredient proportions.

Therefore embodiments of the procedure may comprise determining a representation of the threshold free sugar level in terms of proportions of each ingredient by multiplying a range of proportions of each ingredient by a respective value of free sugar in each ingredient, and then determining the level of free sugar in each set in comparison with the threshold by comparing the possible values of proportions of ingredients, with the representation of the threshold sugar level in terms of the proportions of each ingredient. As expressed later the procedure may therefore determine the intersection of the set of all (physical) solutions with the set of points inside the threshold surface to determine whether or not this is equal to zero, that is whether or not there are any points outside the threshold surface.

However, in some other preferred embodiments the procedure achieves this by determining the maximum free sugar levels out of all possible solutions of the system of simultaneous equations in comparison to the threshold. While it may not be possible to determine a unique solution for the proportions of ingredients when the system is underdetermined, typically one or more elements of the vector of proportions will be defined in terms of (linear) combinations of one or more other elements, which constrains the solution set. The procedure may then employ an approach in which the simultaneous system of equations, along with the constraints that there are no negative proportions of an ingredient and that the proportions (percentages) add up to less than or equal to than unity (100%), are cast as constraints in a constrained optimization problem, where the objective function being optimized is the amount of free sugars in the product. The proportion of each ingredient that maximizes the amount of free sugar in the food, subject to fulfilling the aforementioned constraints, is found, and the total free-sugar amount in the product is calculated from the optimal solution to the problem, and compared to the threshold.

Where the rank of the previously described nutrient matrix and augmented matrix is equal to the number of nutrients a unique solution to the system of simultaneous equations may be possible. This straightforwardly allows determination of the free sugar level from the proportions of ingredients (where a unique physical solution exists). This is similarly true of the modified system of equations previously described.

Where, however, the system is overdetermined as indicated, for example, by the rank of the augmented matrix being greater than the rank of the non-augmented nutrient matrix, the same technique (allowing an additional variable for free sugar) may initially be applied to see whether a solution can be obtained. However if the system is still overdetermined then this indicates a potential problem with the data, for example inconsistent information.

In such a case some preferred embodiments of the procedure determine an approximate solution to the modified system of simultaneous equations, for example a least squares solution. Such an approach may aim to minimise the distance between a product of matrix A and the approximate solution vector x (ingredient nutrient levels and proportions of ingredients), and vector b (empirical nutrient levels). The value of this minimized distance may be used to determine a degree of discrepancy between the estimated nutrient levels in the foodstuff and the empirically measured levels, Where such a discrepancy is small it may merely indicate, for example, an error in the lab data. However where the discrepancy is large, for example greater than an error tolerance, it may indicate a more serious error such as an error in the list of ingredients.

However, in other preferred embodiments, the procedure solves a similar constrained optimization problem as in the underdetermined case, except that now, instead of having the constraint that the simultaneous system of equations be fulfilled, the constraint used is one where the optimal solution, when operated on by the matrix of the ingredient nutrient levels, gives a vector that is different from the vector defining the analysed nutrient levels only by some error tolerance defined by the user.

A difference from the resultant vector and the vector defining the analysed nutrient levels, within error tolerance, may merely indicate, for example, an error in the lab data. However if this difference is not within the error tolerance, it may indicate a more serious error such as an error in the list of ingredients.

The skilled person will appreciate that the determined level of free sugar may be utilised in many ways. For example the procedure may output data defining the determined level of free sugar in relation to a defined threshold level, for example a health-related threshold level, such as a threshold categorising the food or drink into one of a plurality of health categories. Additionally or alternatively the procedure may include marking a container of the item of food or drink to indicate the determined level of free sugar and/or a health category into which the food/drink falls. The container of food or drink may be of any of the usual types including a wrapper, box, tin, carton or the like; the marking may be by printing, affixing an indication, or in any other convenient manner.

In embodiments the method may include analysing the foodstuff or drink to determine the nutrient levels in the food or drink for input to the analysis procedure.

The invention further provides processor control code to implement a method as described above, for example on a general purpose computer system or on a mobile computing device/phone or the like. The code is provided on a non-transitory physical data carrier such as a disk or programmed memory code (and/or data) to implement embodiments of the invention; they comprise source, object or executable code in a conventional programming language (interpreted or compiled), or assembly code or potentially even code for a hardware description language. As the skilled person will appreciate such code and/or data may be distributed between a plurality of coupled components in communication with one another.

In a related aspect the invention further provides data processing apparatus for determining a level of free sugar in a foodstuff or drink, the apparatus comprising: one or more inputs for inputting data defining an ingredient list for said foodstuff or drink, data for an empirical analysis of nutrient levels in said foodstuff or drink, and data defining nutrient levels for each of ingredient in said ingredient list; and a processor coupled to working memory and to program memory; wherein said analysed nutrient levels in said foodstuff or drink are expressible as a combination of a matrix of said ingredient nutrient levels and a vector defining proportions of said ingredients in said ingredient list, representing a system of simultaneous equations defining said analysed nutrient levels in terms of said ingredient proportions and ingredient nutrient levels; and wherein said program memory stores processor control code for controlling said processor to: identify one or more conditions selected from the group consisting of: i) a solution to said system of simultaneous equations is non-physical, ii) said system of simultaneous equations is underdetermined, and iii) said system of simultaneous equations is overdetermined; modify said system of simultaneous equations responsive to said identifying to add an additional ingredient to said ingredient list, said additional ingredient representing an ingredient contributing to sugar content of said foodstuff or drink; and determine a level of free sugar in said foodstuff or drink from said modified system of simultaneous equations.

The data processing apparatus may comprise any suitable apparatus including a processor, for example a general purpose computer system or mobile computer system such as a mobile phone. The program memory may thus comprise, for example, non-volatile storage such as Flash memory or powered volatile memory; embodiments of the data processing apparatus may include one or more network connections. The processor control code may, for example, be in the form of an "App" which may be downloaded to the computing device.

The above described aspects and embodiments of the invention refer particularly to determining a level of free sugar but, aspects and embodiments of the invention may also be employed for determining a level of one or more other substances in food, for example fibre.

BRIEF DESCRIPTION OF THE DRAWINGS

These and other aspects of the invention will now be further described, by way of example only, with reference to the accompanying figures in which:

FIG. 2 shows a diagrammatic illustrations of a solution subspace and a threshold surface illustrating determination of whether or not free sugar is beneath a threshold level in an underdetermined system of equations. The illustrations include a representations of the subspace and surface in a discretized manner, akin to finite-element analysis

DETAILED DESCRIPTION OF PREFERRED EMBODIMENTS

Figure 1:
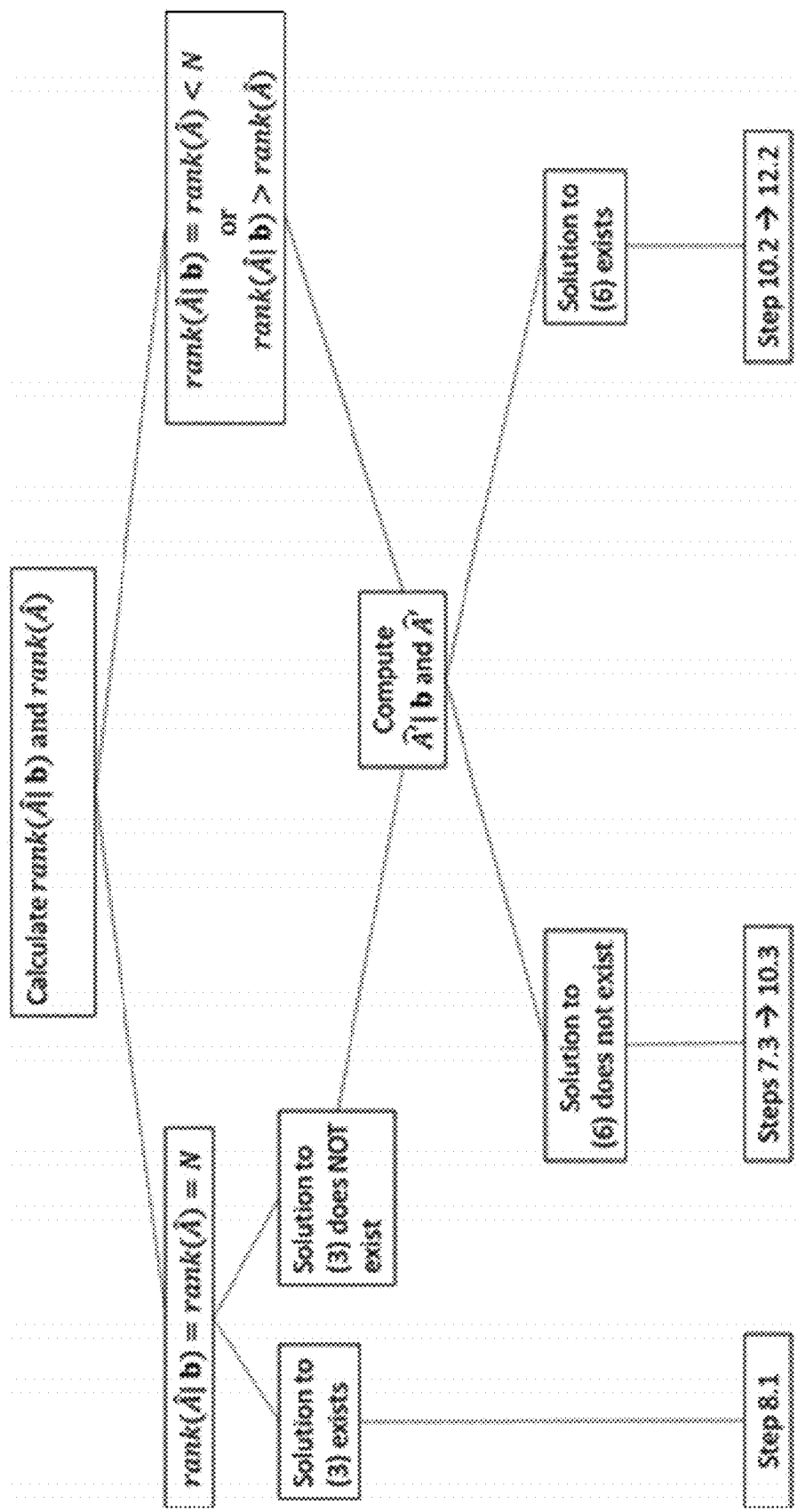
FIG. 1 shows a decision tree for use in embodiments of the invention.

Broadly speaking we will describe systems and methods for evaluating free sugar content from an analytical biochemical "fingerprint" of a food product.

In this specification we refer to "free sugar". Free sugar, which here includes "added sugar", generally refers to sugars such as monosaccharides and disaccharides added to foods and beverages by the manufacturer, cook or consumer, and to sugars naturally present in honey, syrups, fruit juices and fruit juice concentrates. However the techniques we describe are not limited to any particular definition of "free sugar" because the form of mapping employed between food ingredients and the constituents of those ingredients does not depend on what the constituents are defined as. For this reason, in principle, the techniques we describe are not limited to determining free sugar content and could also be employed, for example to determine the level of a particular type of dietary fibre.

Thus we describe a method for determining if a food product's fraction of calories derived from free sugars is below a certain threshold. It involves constructing a biochemical "fingerprint" of the food product from analytical nutrient mass measurements, and solving a non-homogenous linear system that can be constructed with the food product's "fingerprint" and information from publicly available nutrient databases of ingredients.

Given that most health guidelines make specification of a free-sugar threshold, below which foods are considered "healthy," our method can be used by any agency that wishes to determine if food products are below any given free sugar threshold or not.

A biochemical "fingerprint" for the food product is first constructed from analytical nutrient mass measurements, where the fingerprint does not depend on the absolute masses of the nutritional content of the food product, but rather, it depends on the relative amounts of one nutrient to the rest, for all nutrients. Next, a non-homogenous linear system is constructed with the food product's "fingerprint" and information from publicly available nutrient databases of ingredients. This linear system can be described by an augmented matrix, and the rank of the matrix in comparison with the number of nutrients and the rank of the non-augmented matrix can determine if the linear system is either overdetermined, underdetermined, or possesses a unique solution.

Preferred Mode for Carrying Out the Invention

Required Information:
i. Laboratory test of the food product, where the amounts of various nutrients are measured. M will henceforth denote the number of nutrients tested. While the number of different nutrients tested, as well as the identity of each nutrient, is generalized in this method, as an specific example, the following nutrients could be tested with the following tests:
   SUGAR: High performance liquid chromatography (HPLC); Gas chromatography; Paper chromatography; Thin layer chromatography (TLC); Colorimetric tests
   PROTEIN: Kjeldahl or Dumas nitrogen composition tests; Absorbance at A280, Bradford assay; BCA assay; Lowry assay; Biuret test
   FIBRE:
   Gravimetric assay post digestion & washing
   CARBOHYDRATE:
   Digest with enzyme (e.g. alpha-amylase) and measure released mono/oligosaccharides (e.g. by HPAEC-PAD/colorimetric assay)
   FATS:
   Soxhlet extraction, batch solvent or nonsolvent extraction
   WATER
   Drying-weighing (Oven/Microwave/Lyophilisation), Distillation procedure
ii. List of ingredients of a product, where N will henceforth denote the number of ingredients in the product.
iii. An ingredient database which contains the nutrient profile of all ingredients in the food product, where the nutrient profile contains information on all nutrients tested. Such databases are currently publicly available, for example, the following food databases listed in the European Food Information Resource (EuroFir) website could be used [Food Composition Databases. (n.d.). Retrieved Jun. 8, 2016, from http://www.eurofir.org/food-information/food-composition-databases-2/#]

We assume that a food product is being tested to determine if the fraction of its calories derived from free-sugar are below a generalized threshold fraction r. In the following discussion, all vector spaces are assumed to be real Method:
1. All tested nutrients will arbitrarily be assigned an index i, where 1=1, 2, 3, ..., M
2. All ingredients will arbitrarily be assigned an index j, where j=1, 2, 3, ..., N
3. Each constituent ingredient of the product will be classified as a free-sugar containing ingredient, or as a non-free sugar containing ingredient, according to WHO guidelines.
4. The M-dimensional, unitless vector b is constructed, where its vector components $b_i$ are given by $$b_i = \frac{a_i}{\sum_i^M a_i} \quad (1)$$

where $a_i$ is the laboratory-measured amount of the $i^{th}$ nutrient. This unitless vector is the biochemical "fingerprint" of the food product; it does not depend on the absolute masses of the nutritional content of the food product, but rather, it depends on the relative amounts of one nutrient to the rest, for all nutrients 5. The M×N unitless matrix A is constructed, where the matrix elements $A_{ij}$ are given by $$A_{ij} = \frac{a(i|j)}{\sum_i^M a_i} \quad (2)$$

where a(i|j) is the amount of the $i^{th}$ nutrient present in the $j^{th}$ ingredient for mass of the $j^{th}$ ingredient equal to the total mass of the food product tested. This information will be contained in the aforementioned ingredient database.

6. The rank of $\hat{A}$ and the augmented matrix $(\hat{A}|b)$ will be determined. Different scenarios can occur given the properties of the vector b and matrix $\hat{A}$, and different continuations of the procedure described above will be undertaken given the different scenarios. This is illustrated by the "decision tree" shown in FIG. 1.

Progression through this "decision tree" and each scenario will henceforth be explained, Note that progression through the "decision tree" can be straightforwardly automated.

Scenario 1—Single Unique, Physical Solution: rank $(\hat{A}|b)$=rank$(\hat{A})$=N=M In this scenario, the linear system $\hat{A}x=b$ has only one unique solution, where x is a N-dimensional vector whose vector components $x_j$ represent the food product's composition proportions of the $j^{th}$ ingredient. However, a solution with negative vector components is tantamount to negative composition fraction, which corresponds to an unphysical situation and hence an undesirable solution. Moreover, the solution must also conserve mass. Thereby, the following protocol will be undertaken:

7.1 The following linear system will be solved by conventional mathematical methods, such as fraction-free Gaussian elimination:

$$\hat{A}x=b$$

such that $x \varepsilon Q_+^N$ \quad (3)

where $Q_+^N$ is the subset of $Q^N$ where all $x_j \geq 0$ and $$\sum_j^N x_j \leq 1.$$

Given that a solution exists, it will be denoted as $x_M$. $x_M$ gives the only possible (physical) composition proportions that could yield the measured lab results. Solving of the system can be performed computationally via computational libraries such as the Python library SciPy [Jones E, Oliphant E, Peterson P, et al. SciPy: Open Source Scientific Tools for Python, 2001 URL http://www.scipy.org/].

8.1 The fraction of the food product's calories derived from free-sugar will then be calculated with the free-sugar functional $\mathfrak{I}$ defined as:

$$\mathfrak{I}[x] = \frac{\sum_i \sum_j^N 4 \cdot A_{lj} x_j \delta_{jk}}{\sum_i^M \sum_j^N A_{ij} x_j c_i} \quad (4)$$

where $\delta_{jk}$ are Kronecker deltas, k are the indices corresponding to the free-sugar containing ingredients, l are the indices corresponding to all tested saccharide nutrients, and $c_i$ is the amount of calories in the $i^{th}$ nutrient (note that the value of 4 in the denominator corresponds to the amount of calories in sugars).

If $\mathfrak{I}[x_M]$ is below fraction r, less than (r*100)% of the food product's calories are derived from free-sugar.

Finally, the scenario where a solution to (3) does not exist is treated separately below Scenario 2—Lack of Unique, Physical Solution: rank $(\hat{A}|b)$=rank$(\hat{A})\leq N$ or rank$(\hat{A}|b)$>rank$(\hat{A})$ and/or solution to (3) does not exist 7.2 All saccharide nutrients measured in the lab test will be added to the list of ingredients, if they are not already present, and will be classified as free-sugar containing ingredients. N' will henceforth denote the amount of ingredients in the product's modified ingredient list, and all new saccharide "ingredients" will receive an index j such that $N \leq j \leq N'$ 8.2 The M×N' matrix $\widehat{A}'$ is constructed, where the matrix elements $A'_{ij}$ are given by $$A'_{ij} = \frac{a(i|j)}{\sum_i^M a_i} \quad (5)$$

9.2 The ranks of $\widehat{A}'|b$ and $\widehat{A}'$ are calculated. If nk($\widehat{A}'|b$)=rank($\widehat{A}'$)<N', the linear system $\hat{A}'x'=b$ is underdetermined and infinitely many solutions exist; however, if rank($\widehat{A}'|b$)>rank($\widehat{A}'$) then the linear system is overdetermined; no solutions exist.

Note that if rank$(\hat{A}|b)$=rank$(\hat{A})\leq N$ then rank($\widehat{A}'|b$)=rank($\widehat{A}'$)<N': if rank$(\hat{A}|b)$=rank$(\hat{A})$<N, then adding (N'-N) new ingredients can, at most, add N'-N linearly independent columns to the matrices $\hat{A}$ and $\hat{A}|b$, thereby making the maximal possible number of linearly independent columns in both matrices, i.e. the rank of both matrices, to be rank$(\ddot{A})$+(N'-N)=rank$(\hat{A}|b)$+(N'-N)<N+(N'-N)=N'; if rank$(\hat{A}|b)$=rank$(\hat{A})$=N=M, then adding new ingredients.

The procedure for an overdetermined system will be handled separately in Scenario 3.

In what follows, we describe two embodiments of the procedure: the following is the preferred embodiment. After, an alternative embodiment will follow.

10.2 Since the underdetermined system could have infinitely many solutions, simply solving the system for the solution set is not an acceptable option in terms of computational efficiency. Hence, we cast the following problem $$\hat{A}'x'=b$$

such that $x' \varepsilon Q_+^{N'}$ (6)

where x' is an N'-dimensional vector whose vector components $x'_j$ represent the food product's composition proportion of the $j^{th}$ ingredient, as the following constrained optimization problem:

$$\text{maximize } \frac{c^T x'}{d^T x'} \quad (7)$$

subject to $\hat{A}'x' = b$ all $x_j \geq 0$ $$\sum_j^N x_j \leq 1$$

where c and d are vectors whose coefficients correspond to the summation coefficients in $\mathfrak{I}$ (4). Note that $c^T x'$ and $d^T x'$ are affine functions of the $x_j$ variables. Let $x_u$ denote the optimal solution to (7). Essentially, solving (6) is tantamount to a solving (3) where all saccharide's contents are also allowed to vary independently of other nutrients, i.e. we allow for the possibility of unreported added sugars while solving (3).

The solution of (7) $x_u$ maximizes (4), and this maximal value is compared with the free-sugar threshold r. If this maximal value is below the threshold, then it can be unambiguously determined that the amount of free-sugar in the food product does not cross the threshold.

In order to simplify the analysis, the Charnes-Cooper transformation is applied:

$$y = tx', \, t = \frac{1}{d^T x'}$$

which in essence adds a new variable and a new constraint to (7) in order to cast the problem in a simpler form. This transformation translates (7) into the following equivalent constrained optimization problem:

$$\text{maximize } c^T y \quad (8)$$

subject to $\hat{A}'y - bt = 0$ $d^T y = 1$ all $y_j > 0$

-continued $$\sum_{j}^{N} y_j \leq t$$

where, notably, the new variable is t, $d^T y=1$ is an extra constraint not present (7), and all constraints are linear. This linearity feature of (8) allows it to be solved via the Simplex algorithm, a standard algorithm used to solve linear optimization programs. An implementation of this algorithm can be found in SciPy. Once the optimal y is obtained, the optimal x' is given by:

$$x' = \frac{y}{t} \quad (9)$$

11.2 (4) is then calculated with $x_u$; we denote this optimal free-sugar value by $\mathfrak{I}_{u,opt}$. This value can be compared with the free-sugar threshold r; if $\mathfrak{I}_{u,opt} > r$, this signifies that there exists some combination of reported ingredients and unreported added sugars which yield the measured laboratory results and also yield more than (r*100)% of total calories as coming from free-sugars. In this case, one cannot be certain that less than (r*100)% of this food product's total calories are derived from free-sugar. However, $\mathfrak{I}_{u,opt} < r$, then one can be certain that, given the lab results, less than (r*100)% of the food product's calories are derived from free-sugar.

Scenario 3—Inconsistent System: solution to (6) does not exist:

This scenario corresponds to an inconsistent, overdetermined linear system, i.e., NO combination of reported ingredients and unreported added sugars exists which yield the measured laboratory results. If rank($\widehat{A}'$|b)>rank($\widehat{A}'$), then the linear system is overdetermined without the conservation of mass constraints and thereby has no solutions; if rank($\widehat{A}'$|b)=rank($\widehat{A}'$) but a solution to (6) does not exist, then it is the constraints that make the linear system effectively overdetermined.

This corresponds to misreporting of ingredients by the manufacturer or error in the reported laboratory results, both of which result in an impossible calculation. In order to deal with these sources of error, the following procedure will be carried out:

7.3 The following constrained optimization problem will be solved $$\text{maximize } \frac{c^T x'}{d^T x'} \quad (10)$$

subject to $\|\widehat{A}' x' - b\| < \Delta$ all $x_j \geq 0$ $$\sum_{j}^{N} x_j \leq 1$$

where c and d are the same vectors as in (7), and $\Delta$ is some error tolerance allowed by the user. Let $x_o$ denote the optimal solution to (10). Essentially, (10) differs from (7) in how the linear equations $\widehat{A}' x'=b$ are used: in (7), they are enforced as an equality constraint; here, we allow $\widehat{A}' x_o$ to vary from b, which is the laboratory data, by the error tolerance $\Delta$, thereby allowing for some error in the data used in the analysis. Note that if there is no solution which satisfies the constraints of (10), the data used will be deemed to be systematically wrong beyond tolerance.

9.3 We again apply the Charnes-Cooper transformation, which translates (10) into the following equivalent constrained optimization problem:

$$\text{maximize } c^T y \quad (11)$$

subject to $\|\widehat{A}' y - bt\| - \Delta t < 0$ $d^T y = 1$ all $y_j > 0$ $$\sum_{j}^{N} y_j \leq t$$

(11) has the structure of a second order cone programming constrained optimization problem, and thus can be readily solved by standard second-order cone programming algorithms. An implementation of such an algorithm can be found in computational CVXOPT Python library [M. S. Andersen, J. Dahl, and L. Vandenberghe. CVXOPT: A Python package for convex optimization URL at cvxopt.org]

10.3 Given that some $x_o$ can be found, (4) is then calculated with $x_o$; we denote this optimal free-sugar value by $\mathfrak{I}_{o,opt}$. This value can be compared with the free-sugar threshold r; if $\mathfrak{I}_{o,opt} > r$, this signifies that there exists some combination of reported ingredients and unreported added sugars which would yield a biochemical fingerprint whose difference with the measured laboratory biochemical fingerprint is within an acceptable error tolerance, and also yields more than (r*100)% of total calories as coming from free-sugars. In this case, one cannot be certain, to within an appropriate error tolerance, that less than (r*100)% of this food product's total calories are derived from free-sugar. However, $\mathfrak{I}_{u,opt} < r$, then one can be certain that, to within an appropriate error tolerance, less than (r*100)% of the food product's calories are derived from free-sugar.

Now, starting again at step 10.2, what follows is another embodiment of the procedure:

10.2 The following linear system is solved:

$\widehat{A}' x' = b$ such that $x' \in Q_+^{N'}$ (6)

where x' is an N'-dimensional vector whose vector components $x'_j$ represent the food product's composition proportion of the $j^{th}$ ingredient. The set of solutions to (6) will henceforth be referred to as $\{x_u\}$. Note that if rank($\widehat{A}'$|b)=rank($\widehat{A}'$)=N' the linear system only has one unique solution: $\{x_u\}$ will thereby only contain one object if the unique solution fulfils the constraints denoted in (6). However, if rank($\widehat{A}'$|b)=rank($\widehat{A}'$)<N', the undetermined system has many solutions, and $\{x_u\}$ will contain more than one object given that solutions fulfil the constraints denoted in (6).

Essentially, solving (6) is tantamount to a solving (3) where all saccharide's contents are also allowed to vary independently of other nutrients, i.e. we allow for the possibility of unreported added sugars while solving (3). If $\{x_u\}$ is an empty set, this signifies that there are no physical solutions that solve (6); this scenario is treated separately under scenario 3.

11.2 Given that $\{x_u\}$ is not an empty set, the N'-dimensional subset $\aleph$ is then obtained, where all vectors x' in the subset fulfill the conditions:

$$\Im_{[x']} \leq r \text{ and } x' \epsilon Q_+^{N'} \quad (7)$$

12.2 The following set is computed:

$$(Q_+^{N'} - \aleph) \cap \{x_n\} \quad (8)$$

If (8) is not empty, this signifies that there exists some combination of reported ingredients and unreported added sugars which yield the measured laboratory results and also yield more than (r*100)% of total calories as coming from free-sugars. In this case, one cannot be certain that less than (r*100)% of this food product's total calories are derived from free-sugar. However, if (8) is empty, than one can be certain that, given the lab results, less than (r*100)% of the food product's calories are derived from free-sugar.

Note that, for practical reasons, working with $\aleph$ and $\{x_u\}$ will likely be accomplished via discretization of the relevant space into a fine grid (with grid granularity chosen by the user). For computation of $\aleph$, an $N'^{th}$ dimensional array will be computed, where the $i^{th}, j^{th}, k^{th}, \ldots, N'^{th}$ element of the array will be the calculated free sugar value corresponding to the gridpoint: $[i' \cdot g_i, j' \cdot g_j, k' \cdot g_k, \ldots, N''' \cdot g_{N'}]$, where $g_j$ is the chosen granularity of the $j^{th}$ dimension in $Q_+^{N'}$, and where all i', j', k', ... N''' indices range from 0 to $g_j^{-1}$ (a lower bound of 0 ensures the positivity criteria is met). Via conditional statements in a suitable programming language, the gridpoints that do not fulfil the conditions denoted in (7) can be thrown out; the remaining gridpoints yield $\aleph$. Given that many solutions exist, the solution set $\{x_u\}$ can also be discretized by first arbitrarily assigning N'-rank($\hat{A}'$) dimensions as free parameters, discretizing the free parameter dimensions via a chosen dimension granularity as discussed above, and then computing other vector elements via the general solution (obtained from solving the underdetermined linear system) with the various (discrete) free parameter values. Note that, if discretization is undertaken in this manner, then there will be $\prod_j^{N'-rank(\hat{A}')} g_j^{-1}$ elements in the discretised solution set before removal of vectors that do not fulfil the $$\sum_j^N x_j \leq 1$$

criteria.

Via conditional statements, vectors that are not in $Q_+^{N'}$ can then be thrown out, thus yielding $\{x_u\}$. Then, via conditional statements, (8) can be computed.

Scenario 3—Inconsistent System: Solution to (6) does not exist:

This scenario corresponds to an inconsistent, overdetermined linear system, i.e., No combination of reported ingredients and unreported added sugars exists which yield the measured laboratory results. If rank($\hat{A}'$ |b)>rank($\hat{A}'$), then the linear system is overdetermined without the conservation of mass constraints and thereby has no solutions; if rank($\hat{A}'$ |b)=rank($\hat{A}'$) but a solution to (6) does not exist, then it is the constraints that make the linear system effectively overdetermined. This corresponds to misreporting of ingredients by the manufacturer or error in the reported laboratory results, both of which result in an impossible calculation. In order to deal with these sources of error, the following procedure will be carried out:

7.3 Following conventional scientific practice, a constrained least squares solution will be obtained for (6). This can be accomplished via the conjugate gradient method, as described by Branch et. al. [Branch, M. A., Coleman, T. F., & Li, Y. (1999). A subspace, interior, and conjugate gradient method for large-scale bound-constrained minimization problems. *SIAM Journal on Scientific Computing*, 21(1), 1-23.], and can be performed with computational minimization libraries such as the Python library LMFIT [Newville, M., Stensitzki, T., Allen, D. B., & Ingargiola, A. (2014). LMFIT: non-linear least-square minimization and curve-fitting for Python. Zenodo, http://dx.doi.org/10.5281/zenodo, 11813]. This solution will be denoted as $x_{LS}$.

8.3 $\|\hat{A}'x_{LS}-b\|$ will be computed. If this distance value is above an appropriate error tolerance, then the information provided (ingredient list and/or laboratory results) will be deemed to be systematically wrong beyond tolerance.

9.3 Given that $\|\hat{A}'x_{LS}-b\|$ is below the error tolerance, the set $\{x_I\}$ will be obtained, where, for all $x_I$, the distance $\|\hat{A}'x_I-b\|$ is below the error tolerance. Note that the vector $x_{LS}$ is in the $\{x_I\}$ set as well if it fulfills the tolerance criteria. Note that the $\{x_I\}$ set will be centered around $x_{is}$ since this vector is the solution that minimizes the error (given that it fulfils the tolerance criteria).

10.3 The N'-dimensional subset $\aleph$ is then obtained according to (7), and the following set is computed:

$$(Q_+^{N'} - \aleph) \cap \{x_I\} \quad (9)$$

If (9) is not empty, this signifies that there exists some combination of reported ingredients and unreported added sugars which would yield a biochemical fingerprint whose difference with the measured laboratory biochemical fingerprint is within an acceptable error tolerance, and also yields more than (r*100)% of total calories as coming from free-sugars. In this case, one cannot be certain, to within an appropriate error tolerance, that less than (r*100)% of this food product's total calories are derived from free-sugar.

However, if (9) is empty, than one can be certain that, to within an appropriate error tolerance, less than (r*100)% of the food product's calories are derived from free-sugar.

Illustrative Examples on Use of Invention

Scenario 1

Consider a food product with the ingredients: Ingredient A, Ingredient B, Fructose, where only Fructose is a free-sugar containing ingredient. The ingredients' nutrient profile (amount of nutrient per 100 g of ingredient) is shown in Table 1.

TABLE 1

Nutrient profile of ingredients

|  | Ingredient A | Ingredient B | Ingredient C = Fructose |
|---|---|---|---|
| Fructose | 0 g | 25 g | 100 g |
| Fiber | 0 g | 2.5 g | 0 g |
| Protein | 25 g | 0 g | 0 g |
| Lactose | 30 g | 0 g | 0 g |

Moreover, consider the following lab measurement data for 100 g of food product tested: Fructose: 16 g; Fiber: 1.2 g; Protein: 12 g; Lactose: 14.4 g The protocol would be carried out in the following manner:

1. We (arbitrarily) assign the following indices: Fructose→1; Fiber→2; Protein→3; Lactose→4

2. We (arbitrarily) assign the following indices: Ingredient A→1; Ingredient B→2; Ingredient C→3

These two indices assignments thus define $a_i$ and $a(i|j)$ as described above

3. We make the following classifications: Ingredient A→non-free sugar, Ingredient B→non-free sugar; Ingredient C→free sugar containing 4. The vector b, computed according to (1), is thus (rounded to two significant figures):

$$b=[0.37, 0.028, 0.28, 0.33]$$

5. The 4×3 matrix A, constructed according to (2), is thus (rounded to two significant figures):

$$\hat{A} = \begin{bmatrix} 0.00 & 0.00 & 2.29 \\ 0.00 & 0.06 & 0.00 \\ 0.57 & 0.00 & 0.00 \\ 0.69 & 0.00 & 0.00 \end{bmatrix}$$

6. The augmented matrix augmented matrix ($\hat{A}|b$) is given by $$\hat{A}|b = \begin{bmatrix} 0.00 & 0.00 & 2.29 & | & 0.37 \\ 0.00 & 0.06 & 0.00 & | & 0.028 \\ 0.57 & 0.00 & 0.00 & | & 0.28 \\ 0.69 & 0.00 & 0.00 & | & 0.33 \end{bmatrix}$$

The rank of $\hat{A}|b$ and $\hat{A}$ are both calculated to be 3.

7.1 (3) is solved by with the Python numerical library SciPy, yielding:

$$x_M = [0.48, 0.48, 0.04]$$

Indicating that the food product is made from 48% Ingredient A, 48% Ingredient B, and 4% Ingredient C.

8.1 Calculation of $\Im[x_M]$ according to (4) yields:

$$\Im[x_M] = 0.094$$

where it was assumed that fructose, lactose, and protein contain 4 calories per gram, and fiber contains 0 calories per gram.

Scenario 2 (Alternative Embodiment)

Consider a food product with ingredients: Ingredient A, Ingredient B. The ingredients' nutrient profile (amount of nutrient per 100 g of ingredient) is shown in Table 1.

TABLE 1

Nutrient profile of ingredients

|  | Ingredient A | Ingredient B |
|---|---|---|
| Glucose | 10 g | 25 g |
| Fiber | 1 g | 2.5 g |

Moreover, consider the following lab measurement data for 100 g of food product tested: Glucose: 20 g; Fiber: 2 g;

The protocol would be carried out in the following manner:

1. We (arbitrarily) assign the following indices: Glucose→1; Fiber→2
2. We (arbitrarily) assign the following indices: Ingredient A→1; Ingredient B→2.

These two indices assignments thus define $a_i$ and $a(i|j)$ as described above

3. We make the following classifications: Ingredient A→non-free sugar, Ingredient B→non-free sugar 4. The vector b, computed according to (1), is thus (rounded to two significant figures):

$$b=[0.91, 0.091]$$

5. The 2×2 matrix $\hat{A}$, constructed according to (2), is thus (rounded to two significant figures):

$$\hat{A} = \begin{bmatrix} 0.45 & 1.1 \\ 0.045 & 0.11 \end{bmatrix}$$

6. The augmented matrix augmented matrix ($\hat{A}|b$) is given by $$\hat{A}|b = \begin{bmatrix} 0.45 & 1.1 & | & 0.91 \\ 0.045 & 0.11 & | & 0.091 \end{bmatrix}$$

Ranks of $\hat{A}|b$ and $\hat{A}$ are both calculated to be 1.

7.2 The ingredient "glucose" is added to the ingredient list, and given an index of 3

8.2 The 2×3 matrix $\widehat{A'}$, constructed according to (5), is thus $$\hat{A'} = \begin{bmatrix} 0.45 & 1.1 & 4.5 \\ 0.045 & 0.11 & 0 \end{bmatrix}$$

9.2 The ranks of $\widehat{A'}|b$ and $\widehat{A'}$ are both calculated to be 2.

10.2 Solution of (6) via the Python library SimPy yields the set of solutions:

$$\begin{bmatrix} x_1 \\ -0.4x_1 + 0.8 \\ 0 \end{bmatrix}$$

11.2 A plot of (4) evaluated on a grid of the N' dimensional space, with $g_1=0.1$, $g_2=0.1$, $g_3=0.001$ is plotted in FIG. 2(a), where an r of 0.05 was chosen as the upper bound on the computation of (4). The solution set above was discretized by choosing the $x_1$ dimension as a free parameter, with granularity $g_1$ of 0.05, and plotted in FIG. 2(b). Throwing away all gridpoints and solutions which do not fulfil the $$\sum_{j}^{N} x_j \leq 1$$

constraint then yields $\aleph$ and $\{x_u\}$, which are plotted in FIG. 2(c) (i.e. Plots of $\aleph$ and $\{x_u\}$ after filtering of points plotted in 2(a) and 2(b) that do not fulfil conservation of mass constraints ($\{x_u\}$ is plotted as bigger)). For clarity, in FIG. 2(d), the boundary of the subset $\aleph$ (for a chosen r of 0.05) is shown in the triangular-shaped plot (in blue); the region below the plane is the subset $\aleph$, and the set of solutions to (6) are plotted in black.

12. 2 As can be seen from drawing 2, $\{x_u\} \varepsilon \aleph$, therefore yielding ($\square$, $\{x_u\}=\{\ \}$. Therefore, one can be certain that, given the lab results, less than 5% of the food product's calories are derived from free-sugar. Note that, for cases when plotting is impractical, conditional statements with a suitable programming language can yield ($\square$, $\{x_u\}$, thereby automating this part of the calculation as well.

We have thus described a procedure that utilizes analytical nutrient mass measurements and the ingredient list of a food product (found in its nutritional label), in conjunction with publicly available nutrient databases of ingredients, to evaluate free sugar content. This procedure can quantitatively determine, without subjective estimation or reliance on composition percentage information, if either (1) the fraction of calories derived from free sugars in a food product is below a certain threshold, or 2) if such a determination is impossible to make with the available analytical data, or 3) if the ingredient list in the nutritional label is inconsistent with the analytical laboratory data.

The method can use analytical mass measurements of any testable nutrients for the free-sugar evaluation; in particular, non-saccharide analytical data can be used. In fact, given that non free sugar-containing ingredients also contain other testable nutrients in their composition, more analytical information of non-monosaccharide and non-disaccharide nutrients increases the likelihood that outcome (1) described above is achieved, rather than outcome (2). We have also described a method that can leverage mass measurements of non-monosaccharide and non-disaccharide nutrients.

Use of the "fingerprint" helps to ensure that the method produces the same result for two different samples of the same food product if the amounts of sugars relative to other measured nutrients are consistent, even if the absolute masses of different nutrients vary from sample to sample. This helps to ensure that the method is robust against composition percentage changes during manufacturing processes. Moreover, use of the food product's biochemical fingerprint allows the method to be generalized for any mass of food product tested.

Additionally, the procedure is applicable to a food product with any number of ingredients, can use laboratory data with any number of nutrients tested, and can test for adherence to any free-sugar fraction threshold; it is therefore completely generalizable to any amount of data possessed by the user. Additionally, the method can further generalized to evaluate the content of any nutrient, not just saccharide nutrients, relative to some threshold. Furthermore, the method is highly automatable.

No doubt many other effective alternatives will occur to the skilled person. It will be understood that the invention is not limited to the described embodiments and encompasses modifications apparent to those skilled in the art lying within the spirit and scope of the claims appended hereto.

What is claimed is:

1. A method of processing data to determine a level of free sugar in a foodstuff or drink, the method comprising:
    inputting first data defining an ingredient list for said foodstuff or drink;
    laboratory testing said foodstuff or drink, to generate empirical analysis measurements of nutrient levels on said foodstuff or drink;
    inputting second data indicative of the empirical analysis measurements of nutrient levels (b) in said foodstuff or drink;
    inputting third data from a database defining nutrient levels for each of ingredient in said ingredient list;
    wherein said empirical analysis measurements of nutrient levels (b) in said foodstuff or drink are expressible as a combination of a matrix (A) of said ingredient nutrient levels and a vector (x) defining proportions of said ingredients in said ingredient list, representing a system of simultaneous equations defining said analyzed nutrient levels in terms of said ingredient proportions and ingredient nutrient levels; identifying one or more conditions selected from the group consisting of:
    i) a solution to said system of simultaneous equations is non-physical,
    ii) said system of simultaneous equations is underdetermined, and
    iii) said system of simultaneous equations is overdetermined;
    modifying said system of simultaneous equations responsive to said identifying to add one or more additional ingredients to said ingredient list to generate a modified system of simultaneous equations, said one or more additional ingredients representing one or more ingredients contributing to sugar content of said foodstuff or drink; and
    determining a level of free sugar in said foodstuff or drink from said modified system of simultaneous equations, the determining comprising:
    A) if said system of equations is underdetermined, determining said level of free sugar in comparison to a threshold by determining free sugar levels of all possible solutions of said modified system of simultaneous equations in comparison to said threshold;
    B) if said modified system of simultaneous equation has a unique solution defining proportions of said ingredients, the method further comprising determining said level of free sugar in said foodstuff or drink from said defined proportions of ingredients and a level of free sugar in each defined ingredient;
    C) if said system of simultaneous equations is overdetermined and when no unique or exact solution exists to said modified system of simultaneous equations, determining an approximate solution to said modified system of simultaneous equations.

2. A method as claimed in claim 1, wherein if said system of equations is underdetermined, said determining comprises determining sets of possible values of proportions of ingredients and determining said level of free sugar in each set in comparison with said threshold.

3. A method as claimed in claim 2 comprising determining a representation of said threshold sugar level in terms of proportions of each ingredient by multiplying a range of proportions of each ingredient by a respective value of free sugar in each ingredient, and determining said level of free sugar in each set in comparison with said threshold by comparing said possible values of proportions of ingredients with said representation of said threshold sugar level in terms of proportions of each ingredient.

4. A method as claimed in claim 1 wherein identifying when a solution of said system of simultaneous equations is non-physical comprises identifying when one or more of said ingredient proportions is negative and/or when said proportions sum to greater than unity.

5. A method as claimed in claim 1 if said system of simultaneous equations is overdetermined, the method further comprising comparing an estimated set of nutrient levels in said foodstuff or drink determined from said approximate solution with said empirical analysis to determine a degree of discrepancy and, in response, to flag an error when said discrepancy is greater than an error tolerance.

6. A method as claimed in any one of claims 1 and 2-4 further comprising outputting data defining said determined level of free sugar in said foodstuff or drink in relation to a defined threshold level.

7. A method as claimed in any one of claims 1 and 2-4, further comprising categorizing said foodstuff or drink into one of a plurality of health categories dependent upon said determined level of free sugar.

8. A method as claimed in any one of claims 1 and 2-4, further comprising marking a container of said foodstuff or drink to indicate said determined level of free sugar.

9. A method as claimed in any one of claims 1 and 2-4, further comprising analysing said foodstuff or drink to determine said nutrient levels in said foodstuff or drink.

10. A nontransitory computer readable storage medium having data stored therein representing software executable by a computer, the software including instructions to implement the method of any one of claims 1 and 2-4.

11. A system for determining a level of free sugar in a foodstuff or drink, the system comprising:

laboratory testing equipment, configured to generate empirical analysis measurements of nutrient levels on said foodstuff or drink;

one or more inputs for inputting: first data defining an ingredient list for said foodstuff or drink; second data indicative of the empirical analysis measurements of nutrient levels in said foodstuff or drink; and third data from a database defining nutrient levels for each of ingredient in said ingredient list; and a processor coupled to working memory and to program memory;

wherein said empirical analysis measurements of nutrient levels in said foodstuff or drink are expressible as a combination of a matrix of said ingredient nutrient levels and a vector defining proportions of said ingredients in said ingredient list, representing a system of simultaneous equations defining said analyzed nutrient levels in terms of said ingredient proportions and ingredient nutrient levels; and wherein said program memory stores processor control code for controlling said processor to:

identify one or more conditions selected from the group consisting of:

i) a solution to said system of simultaneous equations is non-physical, ii) said system of simultaneous equations is underdetermined, and iii) said system of simultaneous equations is overdetermined;

modify said system of simultaneous equations responsive to said identifying to add one or more additional ingredients to said ingredient list to generate a modified system of simultaneous equations, said one or more additional ingredients representing one or more ingredients contributing to sugar content of said foodstuff or drink; and determine a level of free sugar in said foodstuff or drink from said modified system of simultaneous equations.

* * * * *